United States Patent
Nakano et al.

(10) Patent No.: US 8,702,858 B2
(45) Date of Patent: Apr. 22, 2014

(54) AQUEOUS DISPERSION LIQUID AND COATING MATERIAL, FILM, AND PRODUCT USING THE SAME

(75) Inventors: Kayo Nakano, Yokohama (JP); Akira Sato, Yokohama (JP); Yasuhiro Shirakawa, Yokohama (JP); Keiichi Fuse, Yokohama (JP); Shinya Kasamatsu, Yokohama (JP); Akito Sasaki, Yokohama (JP)

(73) Assignees: Kabushiki Kaisha Toshiba, Tokyo (JP); Toshiba Materials Co., Ltd., Yokohama-Shi (JP)

( * ) Notice: Subject to any disclaimer, the term of this patent is extended or adjusted under 35 U.S.C. 154(b) by 0 days.

(21) Appl. No.: 13/592,741

(22) Filed: Aug. 23, 2012

(65) Prior Publication Data

US 2012/0316056 A1 Dec. 13, 2012

Related U.S. Application Data

(60) Division of application No. 12/874,664, filed on Sep. 2, 2010, now Pat. No. 8,273,169, which is a continuation of application No. PCT/JP2009/000984, filed on Mar. 4, 2009.

(30) Foreign Application Priority Data

Mar. 4, 2008 (JP) .................................. 2008-054139
Apr. 16, 2008 (JP) .................................. 2008-106891

(51) Int. Cl.
*C09D 1/00* (2006.01)
*B01J 23/00* (2006.01)
*C01G 41/02* (2006.01)

(52) U.S. Cl.
USPC ..................... 106/286.2; 106/286.5; 502/305; 423/594.13

(58) Field of Classification Search
USPC ................. 106/286.1–286.7, 287.18–287.19; 252/182.32, 182.33; 502/305–307; 423/594.13, 606
See application file for complete search history.

(56) References Cited

U.S. PATENT DOCUMENTS

| | | | |
|---|---|---|---|
| 5,094,691 | A | 3/1992 | Watanabe et al. |
| 5,188,667 | A | 2/1993 | Watanabe et al. |
| 5,846,505 | A | 12/1998 | Saegusa |
| 6,306,513 | B1 | 10/2001 | Itoh et al. |
| 6,355,694 | B1 | 3/2002 | Suzuki et al. |
| 7,556,682 | B2 | 7/2009 | Koyama et al. |
| 2007/0177372 | A1 | 8/2007 | Matsuda et al. |
| 2008/0006954 | A1 | 1/2008 | Yubuta et al. |
| 2008/0241542 | A1 | 10/2008 | Ohtani et al. |
| 2009/0023583 | A1* | 1/2009 | Nakano et al. ................ 502/309 |

FOREIGN PATENT DOCUMENTS

| | | |
|---|---|---|
| JP | 08-208226 A | 8/1996 |
| JP | 2001-152130 A | 6/2001 |
| JP | 2002-293544 A | 10/2002 |
| JP | 2006-102737 A | 4/2006 |
| JP | 2008-006428 A | 1/2008 |
| JP | 2008-018650 A | 1/2008 |
| WO | WO 2007088891 A1 * | 8/2007 |
| WO | WO 2008/117655 A1 | 10/2008 |

OTHER PUBLICATIONS

JIS R 1701-1, "Fine ceramics (advanced ceramics, advanced technical ceramics)—Test method for air purification performance of photocatalytic materials—Part 1: Removal of nitric oxide", Japanese Industrial Standard, 2004.
Translation of International Preliminary Report on Patentability of PCT/JP2009/000984, dated Oct. 21, 2010, 7 pages.

* cited by examiner

*Primary Examiner* — Anthony J Zimmer
(74) *Attorney, Agent, or Firm* — Foley & Lardner LLP

(57) ABSTRACT

In one embodiment, an aqueous dispersion liquid contains at least one particles selected from tungsten oxide particles and tungsten oxide composite particles. A mean primary particle diameter (D50) of the particles is in the range of 1 nm to 400 nm. In the aqueous dispersion liquid, concentration of the particles is in the range of 0.1 mass % to 40 mass %, and pH is in the range of 1.5 to 6.5. The aqueous dispersion liquid excels in dispersibility of particles and capable of maintaining good liquidity for a long period.

7 Claims, No Drawings

US 8,702,858 B2

AQUEOUS DISPERSION LIQUID AND COATING MATERIAL, FILM, AND PRODUCT USING THE SAME

CROSS-REFERENCE TO RELATED APPLICATION

This application is a divisional of U.S. Ser. No. 12/874,664, filed Sep. 2, 2010, which is a continuation of prior International Application No. PCT/JP2009/000984, filed on Mar. 4, 2009 which is based upon and claims the benefit of priority from Japanese Patent Application No. 2008-054139, filed on Mar. 4, 2008 and No. 2008-106891, filed on Apr. 16, 2008; the entire contents of all of which are incorporated herein by reference.

FIELD

Embodiments described herein relate generally to an aqueous dispersion liquid and a coating material, a film, and a product using the same.

BACKGROUND

Tungsten oxide thin films are widely used as dielectric materials used for electronic devices such as capacitors, filters, and semiconductor chips, and the like, optical element materials used for optical communication filters, isolators, and the like, electrochromic materials used for light control mirrors, and the like, and gas chromic materials used for gas sensors, and the like. Moreover, tungsten oxide is known to function as a visible light responsive photocatalyst material, and is attracting high attention in view of industrial application. Conventionally, the tungsten oxide thin films have been formed by a vacuum deposition method, a sputtering method, a laser ablation method, a sol gel method, and the like.

JP-A 2001-152130 (KOKAI) describes a photocatalyst material obtained by sputter-depositing tungsten oxide on a substrate, where tungsten oxide having a triclinic crystal structure is mainly used. The sputter deposition exposes a substrate to high temperatures, and thus it may be not applicable depending on the heat resistant temperature of the substrate. The sputter deposition is complicated in process management or the like, and not only it becomes costly depending on the shape and size of the substrate, but deposition on a wide area of a building material or the like is difficult. A visible light responsive photocatalyst layer formed of a sputter-deposited tungsten oxide film is excellent in hydrophilicity, but has a problem that its decomposing performance for harmful gas of acetaldehyde and the like is insufficient. Hydrophilicity data under irradiation with visible light are not provided, and thus it is presumed that sufficient photocatalytic performance under visible light is not obtained.

Similarly to the sputtering method, the laser ablation method needs to heat a substrate to high temperatures for controlling crystallinity, and it may be not applicable depending on the heat resistant temperature of the substrate. Not only it becomes costly depending on the shape and size of the substrate, but deposition on a wide area of a building material or the like is difficult. Deposition of tungsten oxide by the sol gel method can be performed relatively inexpensively, but appropriate heating is needed for forming a tungsten oxide film with good crystallinity. Thus, it has constraints on heat resistant temperature of the substrate, shape of the substrate, and so on. When a tungsten oxide film is used as a photocatalyst film which decomposes organic gas or the like, it needs to have an appropriate crystal structure and a large specific surface area, but the sol gel method is not capable of controlling the crystal structure and the specific surface area of the tungsten oxide sufficiently.

A photocatalyst film using a titanium oxide or the like is generally formed by mixing a dispersion liquid obtained by dispersing titanium oxide particles in a dispersion medium with an inorganic binder to prepare a coating material, and applying this coating material on a substrate. The coating material can be applied on various substrates and further can be deposited at around room temperature by selecting a binder, and thus it is possible that the photocatalyst film is applicable to a wide range of products. In the case of a coating material using a dispersion liquid of a photocatalyst powder, it is necessary that particles are well dispersed in the film, for securing performance of the photocatalyst and obtaining film properties of high strength and smoothness. As a typical method to obtain a good dispersion coating material, there is known a method to produce a dispersion liquid in which a photocatalyst powder is dispersed sufficiently in a dispersion medium, and add a binder therein.

Aggregation can easily occur when ultra-fine particles are used like the titanium oxide based photocatalyst, and it is needed to add a finishing agent or a dispersion agent for stabilizing the dispersion state. However, the finishing agent and the dispersion agent are factors to limit photocatalytic performance, and efforts are made to decrease the amount of adding them as much as possible. For example, stabilization of the dispersion state by adding acid and decreasing pH is practiced. Further, lately, there are demands to decrease use amount of volatile organic compounds (VOC) in view of environmental protection, and aqueous dispersion liquids and coating materials using no organic solvent are increasing. Numerous non-ionic compounds are used as a dispersion agent in the aqueous dispersion liquids and coating materials.

When a film using the tungsten oxide powder is formed, first it is necessary to generate fine tungsten oxide particles. As a method of producing a fine tungsten oxide powder, there is known a method to heat an ammonium paratungstate (APT) in the air to obtain a tungsten trioxide powder (see JP-A 2002-293544 (KOKAI)). By the method heating APT in the air, a triclinic tungsten trioxide powder with a primary particle diameter of approximately 0.01 (BET specific surface area=82 $m^2/g$) is obtained. For improving photocatalytic performance of the tungsten trioxide ($WO_3$) powder, it is needed to be in a stable particle state.

By applying disintegration processing, the tungsten trioxide powder can be refined to a certain degree, but it is difficult to have a particle diameter of 100 nm or smaller for example, including aggregated particles. Moreover, when the disintegration processing is applied to make a fine powder, the crystal structure of a fine tungsten trioxide ($WO_3$) powder changes by the stress of the disintegration processing. There occurs a defect to cause re-coupling of electrons and positive holes by stress of the disintegration processing, and thus using it as a photocatalyst conceivably causes decrease in performance. In the production method described in JP-A2002-293544 (KOKAI), kneading of 20 hours or more is needed for stabilizing a BET specific surface area, which poses a problem of low production efficiency of the tungsten trioxide powder.

As a method for obtaining a fine powder efficiently, thermal plasma processing is described in JP-A2006-102737 (KOKAI) for example. By applying the thermal plasma processing, a fine powder with a particle diameter of 1 nm to 200 nm is obtained. Besides the thermal plasma processing, as processing methods capable of oxidizing a tungsten material while sublimating it in an oxygen atmosphere, there are known arc discharge processing, laser processing, electron ray processing, gas burner processing, and the like. However, when a fine tungsten oxide powder produced by applying these methods is used as it is as a photocatalyst, there may be a case where optical characteristics and crystal structure are not optimum, and sufficient photocatalyst characteristics cannot always be obtained. Therefore, for forming a photocatalyst film, it is necessary to perform control to have appropriate optical characteristics, crystal structure, and particle diameter in a powder state.

For forming a stable dispersion liquid using the tungsten oxide particles, it is important not only to use tungsten oxide particles with a fine primary particle diameter, but also to facilitate decomposition of, for example, aggregated particles and prevent re-aggregation. However, under the current situation, a dispersion liquid and a coating material in which the tungsten oxide particles do not separate or precipitate for a long period have not been obtained. Particularly, when the tungsten oxide particles are applied to a photocatalyst, the dispersion liquid and the finishing agent become a factor to limit photocatalytic performance. Thus, a small amount of the dispersion liquid or the finishing agent is added, or a dispersion liquid to which it is not necessary to add them is desired. However, sufficient performance has not been obtained with such a dispersion liquid or a coating material.

DETAILED DESCRIPTION

In one embodiment, an aqueous dispersion liquid contains at least one particles selected from tungsten oxide particles and tungsten oxide composite particles. A mean primary particle diameter (D50) of the particles is in a range of 1 nm to 400 nm, concentration of the particles is in a range of 0.1 mass % to 40 mass %, and pH is in a range of 1.5 to 6.5.

In one embodiment, a coating material contains the aqueous dispersion liquid of the embodiment, and at least one binder component selected from an inorganic binder and an organic binder. In one embodiment, a film is formed by applying the aqueous dispersion liquid of the embodiment or the coating material of the embodiment on a substrate. In one embodiment, a product includes a film of the embodiment.

An aqueous dispersion liquid according to an embodiment contains at least one particles selected from tungsten oxide particles and tungsten oxide composite particles (hereinafter referred to as tungsten oxide based particles). The tungsten oxide based particles contained in the aqueous dispersion liquid have a mean primary particle diameter (D50) in the range of 1 nm to 400 nm. In the aqueous dispersion liquid, concentration of the tungsten oxide based particles is in the range of 0.1 mass % to 40 mass %, and pH is in the range of 1.5 to 6.5. The aqueous dispersion liquid is used for forming a covering film, a coating film, or the like containing the tungsten oxide based particles.

The aqueous dispersion liquid is not limited to one such that tungsten oxide particles are dispersed in water, and may be one such that tungsten oxide composite particles are dispersed in water. The tungsten oxide composite is one such that tungsten oxide as a main constitute contains a transition metal element and/or other metal elements. The transition metal element is an element with an atomic number from 21 to 29, 39 to 47, 57 to 79, or 89 to 109. It is preferred that the tungsten oxide composite include at least one metal element selected from Ti, Zr, Mn, Fe, Pd, Pt, Cu, Ag, Al, and Ce.

It is preferred that the content of the metal element in the tungsten oxide composite be in the range of 0.001 mass % to 50 mass %. When the content of the metal element is more than 50 mass %, it is possible that the characteristics of the tungsten oxide particles decrease. It is more preferred that the content of the metal element be 10 mass % or less. The lower limit value of the content of the metal element is not particularly limited, but it is preferred that the content thereof be 0.001 mass % or more, more preferably 0.01 mass % or more. For avoiding decrease of dispersibility of the aqueous dispersion liquid, it is preferred that the content and form of the metal element be adjusted so as not to cause a large change in pH and zeta potential. Considering such points, it is preferred that the content of the metal element be 2 mass % or less.

In the tungsten oxide composite used for the aqueous dispersion liquid, the metal element may exist in various forms. The tungsten oxide composite can include a metal element in the form of a single metal element, a compound including a metal element (compound including oxide), a complex compound of tungsten oxide, or the like. The metal element included in the tungsten oxide composite may itself form a compound with other elements. An example of a typical form of the metal element is oxide. The metal element is mixed with, for example, a tungsten oxide powder in the form of a single element, a compound, a complex compound, or the like. The metal element may be carried by the tungsten oxide.

The method of combining the tungsten oxide with the metal element (specifically a single element, a compound, or a complex compound of at least one element selected from Ti, Zr, Mn, Fe, Pd, Pt, Cu, Ag, Al, and Ce) is not particularly limited, and various combining methods such as a mixing method to mix powders with each other, an impregnation method, a carrying method, and so on can be applied. A typical combining method is described below. An example of a method of combining copper with tungsten oxide is a method to mix a tungsten oxide powder with a copper oxide powder. Another effective method is such that the tungsten oxide powder is added and mixed in an aqueous solution of copper nitrate or copper sulfate or in an ethanol solution, dried thereafter to temperatures from 70° C. to 80° C., and burned at temperatures from 500° C. to 550° C.

Further, it is also possible to apply a method to disperse a tungsten oxide powder in an aqueous copper chloride solution or an aqueous copper sulfate solution, and dry this dispersion liquid (impregnation method). The impregnation method is not limited to a method of combining copper, and can be applied to a method of combining iron using an aqueous iron chloride solution, a method of combining silver using an aqueous silver chloride solution, a method of combining platinum using an aqueous platinum chloride solution, a method of combining palladium using an aqueous palladium chloride solution, and the like. Moreover, tungsten oxide may be combined with a metal element (oxide) using an oxide sol such as a titanium oxide sol or an alumina sol. Besides them, various combining methods can be applied.

It is preferred that the tungsten oxide based particles used for the aqueous dispersion liquid be in a state of having a stable crystal structure. If the crystal structure is unstable, when the aqueous dispersion liquid is stored for a long period, it is possible that the crystal structure of the tungsten oxide based particles changes, and thereby its liquidity changes and dispersion state decreases. Furthermore, the tungsten oxide based particles may contain metal elements or the like as a minute amount of impurity. It is preferred that the content of metal elements as impurity elements be 2 mass % or less. As the impurity metal elements, there are elements generally included in a tungsten ore and contamination elements or the like which are mixed in when a tungsten compound or the like used as a raw material is produced, and examples include Fe, Mo, Mn, Cu, Ti, Al, Ca, Ni, Cr, Mg, and so on. It is not applicable when these elements are used as component elements of a composite.

The mean primary particle diameter (D50) of the tungsten oxide based particles used for the aqueous dispersion liquid is in the range of 1 nm to 400 nm. It is preferred that a BET specific surface area of the tungsten oxide based particles be in the range of 4.1 m$^2$/g to 820 m$^2$/g. Particles before dispersion or particles resulted from drying a dispersion liquid are estimated by SEM, TEM, or the like, and the mean primary particle diameter (D50) is obtained based on a mean particle diameter (D50) of integrated diameters with reference to volumes of particles with n being 50 or more from an image analysis of a picture. The mean primary particle diameter (D50) may match the mean particle diameter converted from the specific surface area.

In order to generate a stable dispersion liquid to obtain a uniform film (a film containing the tungsten oxide based particles), it is better that the primary particle diameter is small and the specific surface area is large. Therefore, when the mean primary particle diameter of the tungsten oxide based particles is larger than 400 nm, or when the BET specific surface area is smaller than 4.1 m$^2$/g, it is not possible to obtain sufficient characteristics as a dispersion liquid. On the other hand, when the mean primary particle diameter of the tungsten oxide based particles is smaller than 1 nm or when the BET specific surface area is larger than 820 m$^2$/g, the particles are too small and provide poor handleability as a powder. Therefore, practicability of the powder and the dispersion liquid using this powder decreases.

When the tungsten oxide based particles are used as a photocatalyst powder, generally the larger the specific surface area and the smaller the particle diameter, the higher the performance of the photocatalyst powder. Therefore, when the mean primary particle diameter of the tungsten oxide based particles is larger than 400 nm or when the BET specific surface area is smaller than 4.1 m$^2$/g, the photocatalytic performance of the tungsten oxide based particles decreases, and it is difficult to form a uniform and stable film. The photocatalytic performance decreases also in this point. When the mean primary particle diameter of the tungsten oxide based particles is too small, the dispersibility decreases and it is difficult to produce a uniform dispersion liquid.

It is preferred that the mean primary particle diameter of the tungsten oxide based particles be in the range of 2.7 nm to 75 nm, more preferably in the range of 5.5 nm to 51 nm. It is preferred that the BET specific surface area be in the range of 11 m$^2$/g to 300 m$^2$/g, more preferably in the range of 16 m$^2$/g to 150 m$^2$/g. When the primary particle diameter of the tungsten oxide based particles is too small, the dispersibility decreases as described above. For improving this point, it is preferred that the mean primary particle diameter of the tungsten oxide based particles be 5.5 nm or larger.

The concentration of the tungsten oxide based particles in the aqueous dispersion liquid is in the range of 0.1 mass % to 40 mass %. When the concentration is less than 0.1 mass %, the content of the tungsten oxide based particles is insufficient, and desired performance cannot be obtained. When the concentration is higher than 40 mass %, the tungsten oxide based particles exist in an adjacent state when they become a film, and the surface area for exhibiting performance cannot be obtained. Accordingly, not only the sufficient performance cannot be exhibited, but also the cost is increased because the tungsten oxide based particles are included more than necessary.

It is preferred that the concentration of the tungsten oxide based particles is in the range of 1 mass % to 20 mass %, more preferably in the range of 1 mass % to 10 mass %. A high-concentration dispersion liquid containing the tungsten oxide based particles by 20 mass % or more is capable of easily achieving a state that the tungsten oxide based particles are uniformly dispersed when it is diluted to produce a coating material. It has an advantage that a coating material in which the tungsten oxide based particles are uniformly dispersed can be produced.

Moreover, the pH of the aqueous dispersion liquid is in the range of 1.5 to 6.5. In the aqueous dispersion liquid containing the tungsten oxide based particles, the zeta potential is negative with pH being in the range of 1.5 to 6.5, and thus an excellent dispersed state can be achieved. Such a dispersion liquid and a coating material using this liquid can be applied on a substrate or the like thinly without having unevenness. The pH of the aqueous dispersion liquid has a correlation with the concentration of the tungsten oxide based particles. The dispersion state changes when the pH changes, and good dispersibility is obtained when pH is in the range of 1.5 to 6.5.

When the pH of the aqueous dispersion liquid is smaller than 1.5, the zeta potential gets close to zero, and thus the dispersibility decreases. When the pH of the aqueous dispersion liquid is larger than 6.5, it becomes close to the alkaline side, and the tungsten oxide becomes liable to dissolve. To adjust the pH of the aqueous dispersion liquid, an acid or alkaline solution of hydrochloric acid, sulfuric acid, tetramethylammonium hydroxide (TMAH), ammonia, sodium hydroxide, and the like may be added as necessary. It is preferred that the pH of the aqueous dispersion liquid be in the range of 2.0 to 6.0, more preferably in the range of 2.5 to 5.5.

With the pH of the aqueous dispersion liquid being in the range of 2.5 to 5.5, photocatalytic performance (gas decomposing performance) can be exhibited more effectively. After the aqueous dispersion liquid having pH in the range of 2.5 to 5.5 is applied and dried, when the surface state of particles is observed by a FT-IR (Fourier-transform infrared absorption spectroscopy), absorption of hydroxyl can be seen in the vicinity of 3700 cm$^{-1}$. Using such a film as a photocatalyst film, it is possible to obtain excellent organic gas decomposing performance.

When the aqueous dispersion liquid having pH adjusted to 6 is applied and dried, the absorption of hydroxyl decreases, and the gas decomposing performance decreases as well. When the pH of the aqueous dispersion liquid is adjusted to 2, although the hydroxyl exists, the dispersibility slightly decreases due to that the zeta potential gets close to zero, and the gas decomposing performance decreases slightly.

In the aqueous dispersion liquid of this embodiment, particle size distribution of the tungsten oxide based particles is preferably such that the D90 diameter is in the range of 0.01 µm to 10 µm. The aqueous dispersion liquid is produced by mixing particles with a dispersion medium, and performing dispersion processing with an ultrasonic dispersion machine, a wet jet mill, a beads mill, or the like. In the aqueous dispersion liquid obtained in this manner, the tungsten oxide based particles include aggregated particles, which are aggregated primary particles. The particle size distribution is measured with a wet laser diffraction particle size distribution analyzer or the like including the aggregated particles, and when the D90 diameter in integrated diameters with reference to volumes is in the range of 0.01 µm to 10 µm, a good distribution state and an even and stable film formability can be obtained.

When the D90 diameter of the particle size distribution of the tungsten oxide based particles is smaller than 0.01 µm, the entire particle size of the tungsten oxide based particles is too small, and thus the dispersibility decreases. Accordingly, it becomes difficult to obtain a uniform dispersion liquid or coating material. When the D90 diameter is larger than 10 μm, it becomes difficult to form a uniform and stable film. Particularly, when the tungsten oxide based particles have the photocatalytic performance, it is not possible to exhibit this photocatalytic performance sufficiently.

It is preferred that the D90 diameter in the particle size distribution of the aqueous dispersion liquid be in the range of 0.01 μm to 1 μm, more preferably in the range of 0.01 μm to 0.1 μm. In order to form a uniform and smooth film or a film with high strength, it is preferred that the aggregated particles be disintegrated as much as possible to make the D90 diameter smaller. When the tungsten oxide based particles have the photocatalytic performance, for exhibiting the photocatalytic performance after the film is formed, conditions not to give too much distortion to particles in the dispersion processing are set preferably. In order to form a uniform and stable film using an aqueous dispersion liquid or a coating material having good dispersibility, application by a method such as spin coating, dipping, spraying, or the like is preferred.

When the color of the aqueous dispersion liquid is expressed by the L*a*b color system, it is preferred that the aqueous dispersion liquid have a color in the range of a* of 10 or less, b* of −5 or more, and L* of 50 or more. By applying a dispersion liquid having such a color tone on a substrate and forming a film, good photocatalytic performance can be obtained, and additionally, the color of the substrate will not be impaired. Therefore, it becomes possible to obtain a coating material or a film.

The aqueous dispersion liquid of this embodiment may contain alcohol in the range of 20 mass % or less as a dispersion medium other than water. As the alcohol, for example, methanol, ethanol, 1-propanol, 2-propanol, or the like is used. When the content of the alcohol is more than 20 mass %, aggregation easily occurs. It is preferred that the content of the alcohol be 10 mass % or less. The aqueous dispersion liquid may be such that the tungsten oxide based particles are dispersed in an aqueous dispersion medium in a state that they are mixed with, carried on, or impregnated in a material having absorption performance such as activated carbon, zeolite, or the like.

It is preferred that the tungsten oxide based particles (powder) used for the aqueous dispersion liquid in this embodiment be produced by the following method, but it is not limited thereto. It is preferred that the tungsten oxide based particles be produced applying a sublimation process. Further, combining a heat treatment process with the sublimation process is also effective. With tungsten trioxide based particles produced by such a method, the above-described mean primary particle diameter, BET specific surface area, and crystal structure can be achieved stably. Moreover, the mean primary particle diameter approximates to the value converted from the BET specific surface area, and particles with small dispersion in particle diameter (fine powder) can be obtained stably.

The sublimation process will be described. The sublimation process is a process in which tungsten trioxide particles are obtained by sublimating a metal tungsten powder, a tungsten compound powder, or a tungsten compound solution in an oxygen atmosphere. The sublimation is a phenomenon that a state change from a solid phase to a vapor phase, or from a vapor phase to a solid phase occurs without undergoing a liquid phase. The tungsten oxide powder can be obtained by oxidizing the metal tungsten powder, tungsten compound powder, or tungsten compound solution as a raw material while sublimating it.

Any one of the metal tungsten powder, tungsten compound powder, and the tungsten compound solution may be used as the raw material (tungsten material) in the sublimation process. Examples of the tungsten compound used as the raw material include tungsten trioxide ($WO_3$), tungsten dioxide ($WO_2$), tungsten oxide of a low-grade oxide or the like, tungsten carbide, ammonium tungstate, calcium tungstate, tungstic acid, and the like.

By performing the sublimation process of the tungsten raw material as described above in the oxygen atmosphere, the metal tungsten powder or the tungsten compound powder is turned from a solid phase to a vapor phase instantly, and further the metal tungsten vapor turned to a vapor phase is oxidized, to thereby obtain tungsten oxide particles. Even when the solution is used, it turns to a vapor phase after being tungsten oxide or compound. Thus, the tungsten oxide particles can be obtained using oxidation reaction in a vapor phase. Moreover, the crystal structure of the tungsten oxide particles can be controlled.

As the raw material for the sublimation process, preferably at least one selected from a metal tungsten powder, a tungsten oxide powder, a tungsten carbide powder, and an ammonium tungstate powder is used since the tungsten oxide particles obtained by sublimation in the oxygen atmosphere hardly include impurities. The metal tungsten powder and the tungsten oxide powder are preferred particularly as raw materials for the sublimation process since they do not include any harmful by-product (substance other than the tungsten oxide) formed in the sublimation process.

As the tungsten compound used for the raw material, a compound including tungsten (W) and oxygen (O) as its constituent elements is preferred. Including W and O as constituent elements makes it easy to be sublimated instantly when inductively-coupled plasma processing or the like described later is applied in the sublimation process. Examples of such a tungsten compound include $WO_3$, $W_{20}O_{58}$, $W_{18}O_{49}$, $WO_2$, and the like. Further, a solution, salt, or the like of tungstic acid, ammonium paratungstate, or ammonium metatungstate, is also effective.

When the tungsten oxide composite particles are produced, a transition metal element or other elements may be mixed in the form of metal, compound including oxide, complex compound, or the like, in addition to the tungsten material. By processing the tungsten oxide with other elements at once, complex compound particles of complex oxide of the tungsten oxide and other elements, or the like can be obtained. The tungsten oxide composite particles can also be obtained by mixing the tungsten oxide particles with or carrying them on single particles or compound particles of other metal elements. The method of combining the tungsten oxide with other metal elements is not particularly limited, and it is possible to apply various publicly known methods.

It is preferred that the metal tungsten powder or the tungsten compound powder as the tungsten material have a mean particle diameter in the range of 0.1 μm to 100 μm. The mean particle diameter of the tungsten material is more preferably in the range of 0.3 μm to 10 μm, furthermore preferably in the range of 0.3 μm to 3 μm, desirably in the range of 0.3 μm to 1.5 μm. When the metal tungsten powder or the tungsten compound powder having the mean particle diameter in the above ranges is used, sublimation occurs easily.

When the mean particle diameter of the tungsten material is smaller than 0.1 μm, the raw material powder is too fine. Thus, pre-adjustment of the raw material powder becomes necessary, handleability decreases, and additionally the cost increases, thereby making it unfavorable in an industrial aspect. When the mean particle diameter of the tungsten material is larger than 100 μm, uniform sublimation reaction does not occur easily. Even when the mean particle diameter is large, processing with a large energy amount can cause uniform sublimation reaction, but this is unfavorable in an industrial aspect.

An example of the method of sublimating the tungsten material in the oxygen atmosphere in the sublimation process is at least one processing selected from inductively coupled plasma processing, arc discharge processing, laser processing, electron beam processing, and gas burner processing. Among them, in the laser processing or the electron beam processing, laser or electron beam is irradiated to perform the sublimation processing. The laser or electron beam has a small irradiation spot diameter, and thus it takes time to process a large amount of raw material at once. However, they have an advantage that it is not necessary to strictly control the particle diameter or stability of supply amount of the raw material powder.

The inductively coupled plasma processing or the arc discharge processing needs adjustment of a generating area of plasma or arc discharge, but it is capable of allowing oxidation reaction of a large amount of raw material powder to occur at once in the oxygen atmosphere. Further, the amount of raw material to be processed at once can be controlled. The gas burner processing needs a relatively low power cost, but it is difficult to process a large amount of raw material powder or raw material solution. Accordingly, the gas burner processing is inferior in productivity. In addition, the gas burner processing may be one having sufficient energy for causing sublimation, and is not particularly limited. A propane gas burner, an acetylene gas burner, or the like is used.

When the inductively coupled plasma processing is applied to the sublimation process, generally there is used a method in which plasma is generated using argon gas or oxygen gas, and the metal tungsten powder or the tungsten compound powder is supplied into this plasma. Examples of the method of supplying the tungsten material into the plasma include a method to blow the metal tungsten powder or the tungsten compound powder together with carrier gas, a method to spray a dispersion liquid in which the metal tungsten powder or the tungsten compound powder is dispersed in a predetermined liquid dispersion medium.

Examples of the carrier gas used when the metal tungsten powder or the tungsten compound powder is blown into the plasma include air, oxygen, inert gas containing oxygen, and the like. Among them, the air is used preferably because of its low cost. When oxygen is contained enough in the reaction field, like in the case where reaction gas including oxygen is supplied other than the carrier gas, the case where the tungsten compound powder is the tungsten trioxide, or the like, inert gas such as argon or helium may be used as the carrier gas. For the reaction gas, preferably oxygen, inert gas including oxygen, or the like is used. When the inert gas including oxygen is used, preferably the oxygen amount is set so that it is possible to sufficiently supply a necessary oxygen amount for oxidation reaction.

By applying the method of blowing the metal tungsten powder or the tungsten compound powder together with carrier gas, and adjusting the gas flow rate or the pressure in a reaction container, the crystal structure of the tungsten trioxide particles can be controlled easily. Specifically, it is easy to obtain tungsten trioxide particles having a crystal structure of at least one selected from monoclinic crystal and triclinic crystal (monoclinic crystal, triclinic crystal, or mixed crystal of monoclinic crystal and triclinic crystal) or one in which rhombic crystal is mixed therewith. It is preferred that the crystal structure of the tungsten trioxide particles be a mixed crystal of monoclinic crystal and triclinic crystal or a mixed crystal of monoclinic crystal, triclinic crystal, and rhombic crystal.

An example of the dispersion medium used for producing the dispersion liquid of the metal tungsten powder and the tungsten compound powder is a liquid dispersion medium having oxygen atoms in molecules. Using the dispersion liquid facilitates handling of the raw material powder. As the liquid dispersion medium having oxygen atoms in molecules, for example, there is used one including at least one selected from water and alcohol by 20 capacity % or more. As the alcohol used as the liquid dispersion medium, for example, at least one selected from methanol, ethanol, 1-propanol, and 2-propanol is preferred. Since water and alcohol easily evaporate by heat of plasma, they do not hinder sublimation reaction or oxidation reaction of the raw material powder, and they easily facilitate oxidation reaction because they contain oxygen in molecules.

When the metal tungsten powder or the tungsten compound powder is dispersed in the dispersion medium to produce the dispersion liquid, it is preferred that the metal tungsten powder or the tungsten compound powder be included in the range of 10 mass % to 95 mass %, more preferably in the range of 40 mass % to 80 mass % in the dispersion liquid. By dispersing in the dispersion liquid in such a range, the metal tungsten powder or the tungsten compound powder can be dispersed uniformly in the dispersion liquid. When it is dispersed uniformly, uniform sublimation reaction of the raw material powder can occur easily. When the content in the dispersion liquid is less than 10 mass %, the amount of the raw material powder is too small, and it cannot be produced efficiently. When the content is more than 95 mass %, the amount of the dispersion liquid is small, the viscosity of the raw material powder increases and makes it sticky to the container, and thus the handleability decreases.

By applying the method to have the metal tungsten powder or the tungsten compound powder in the dispersion liquid and blowing it into plasma, the crystal structure of the tungsten trioxide particles can be controlled easily. Specifically, tungsten trioxide particles having a crystal structure of at least one selected from monoclinic crystal and triclinic crystal or one in which rhombic crystal is mixed therewith can be obtained easily. Further, also by using a tungsten compound solution as the raw material, the sublimation reaction can be performed uniformly, and moreover, controllability of the crystal structure of the tungsten trioxide particles improves. The method using the dispersion liquid as described above is also applicable in the arc discharge processing.

When the sublimation process is performed by irradiating with laser or electron beam, preferably pelletized metal tungsten or tungsten compound is used as the raw material. The laser or electron beam has a small irradiation spot diameter, and thus supply becomes difficult when the metal tungsten powder or the tungsten compound powder is used. However, using the pelletized metal tungsten or tungsten compound makes it possible to perform sublimation efficiently. The laser may be one having sufficient energy for sublimating the metal tungsten or the tungsten compound and is not particularly limited, but $CO_2$ laser is preferred because of its high energy.

When the pellets are irradiated with the laser or electron beam, moving at least one of the irradiation source of the laser light or electron beam and the pellets enables to effectively sublimate the entire surface of a pellet having a certain degree of size. This makes it easy to obtain the tungsten trioxide powder having a crystal structure in which rhombic crystal is mixed with at least one selected from monoclinic crystal and triclinic crystal. The pellets as described above are also applicable in the inductively coupled plasma processing and the arc discharge processing.

The tungsten oxide based particles used for the aqueous dispersion liquid of this embodiment can be obtained just by the sublimation process as described above, but it is also effective to perform heat treatment process on the tungsten oxide based particles produced in the sublimation process. The heat treatment process is to heat treat the tungsten trioxide based particles obtained in the sublimation process at predetermined temperatures and for predetermined time in an oxidative atmosphere. Also in the case where the tungsten trioxide particles cannot be formed sufficiently by condition control or the like in the sublimation process, the percentage of the tungsten trioxide particles in the tungsten oxide particles can be 99% or more, substantially 100%, by performing the heat treatment. Moreover, the crystal structure of the tungsten trioxide particles can be adjusted to a predetermined structure in the heat treatment process.

Examples of the oxidative atmosphere used in the heat treatment process include air and oxygen-containing gas. The oxygen-containing gas means inert gas containing oxygen. It is preferred that the heat treatment temperature be in the range of 200° C. to 1000° C., more preferably 400° C. to 700° C. It is preferred that the heat treatment time be in the range of 10 minutes to 5 hours, more preferably 30 minutes to 2 hours. By having the temperature and time of the heat treatment process in the above-described ranges, the tungsten trioxide can be formed easily from tungsten oxide other than the tungsten trioxide. Further, to obtain a powder with less defects and good crystallinity, it is preferred that temperature increase or temperature decrease during heat treatment be performed gradually. Rapid heating or cooling during heat treatment leads to decrease of crystallinity.

When the heat treatment temperature is lower than 200° C., it is possible that an oxidation effect for turning a powder which did not become the tungsten trioxide in the sublimation process to the tungsten trioxide is not obtained sufficiently. When the heat treatment temperature is higher than 1000° C., the tungsten oxide particles grow rapidly, and thus the specific surface area of the obtained fine tungsten oxide powder can decrease easily. Moreover, by performing the heat treatment process at the temperatures and for the time as described above, it is possible to adjust the crystal structure and crystallinity of the fine tungsten trioxide powder.

The aqueous dispersion liquid in this embodiment can be used as a film forming material in the state as it is. The aqueous dispersion liquid is mixed with a binder component or the like to produce a coating material, and this coating material may be used as a film forming material. The coating material contains at least one binder component selected from an inorganic binder and an organic binder together with the aqueous dispersion liquid. It is preferred that the content of the binder component be in the range of 5 mass % to 95 mass %. When the content of the binder component is more than 95 mass %, it is possible that desired photocatalytic performance cannot be obtained. When the content of the binder component is less than 5 mass %, sufficient coupling force cannot be obtained, and the film characteristics may decrease. By applying such a coating material, strength, hardness, adhesion strength to the substrate, and the like of the film can be adjusted to a desired state.

As the organic binder, for example, there is used a product obtained by decomposing a hydrolytic silicon compound such as an alkyl silicate, a silicon halide, and a partial hydrolytic product of them, an organic polysiloxane compound or a polycondensate thereof, silica, colloidal silica, water glass, a silicon compound, phosphate such as zinc phosphate, metal oxide such as zinc oxide or zirconium oxide, dense phosphate, cement, gypsum, lime, frit for enamel, or the like. As the organic binder, for example, there is used fluorine based resin, silicone resin, acrylic resin, epoxy resin, polyesterresin, melamine resin, urethane resin, alkyd resin, or the like.

By applying the aqueous dispersion liquid or the coating material as described above on the substrate, a film containing the tungsten oxide based particles can be formed stably and uniformly. As the substrate on which such a film is formed, a glass, a ceramic, a plastic, a resin such as acrylic resin, a paper, a fiber, a metal, a wood, or the like is used. It is preferred that the film thickness be in the range of 2 nm to 1000 nm. When the film thickness is smaller than 2 nm, it is possible that the state that the tungsten oxide based particles exist uniformly is not obtained. When the film thickness is larger than 1000 nm, adhesion strength to the substrate decreases. It is preferred that the film thickness be in the range of 2 nm to 400 nm.

It is preferred that the film of this embodiment have the photocatalytic performance under irradiation with visible light. Generally, the visible light is light having a wavelength in the region of 380 nm to 830 nm, and is light irradiated from a general illumination, such as a white fluorescent light, sunlight, a white LED, an electric bulb, a halogen lamp, or a xenon lamp, or a blue light emitting diode, a blue laser, or the like as a light source. The film in this embodiment exhibits the photocatalytic performance in an ordinary indoor environment. The photocatalytic performance is an operation such that upon absorption of light, a pair of electron and positive hole is excited with respect to one photon, and the excited electron and positive hole activate hydroxyl or acid at the surface by oxidation-reduction, and an active oxygen species generated by this activation oxidatively decomposes organic gas and the like, and is further an operation to exhibit hydrophilicity, antibacterial/disinfection performance, and the like.

A product of this embodiment includes a film formed using the aqueous dispersion liquid or the coating material described above. Specifically, the film is formed by applying the aqueous dispersion liquid or the coating material on the surface of the substrate constituting the product. The film formed on the substrate surface may contain a zeolite, an activated carbon, a porous ceramic, or the like. The photocatalyst film described above and the product including this film are characterized in that they excel in decomposing performance for organic gas such as acetaldehyde and formaldehyde under irradiation with visible light, and especially exhibit high activity even under low illuminance. The film of this embodiment exhibits hydrophilicity by contact angle measurement with water. Moreover, the film exhibits high antibacterial performance in antibacterial performance estimation against staphylococcus aureus bacteria or colon bacillus under irradiation with visible light.

Specific examples of the product including the film of this embodiment include air-conditioners, air cleaning devices, electric fans, refrigerators, microwave ovens, dishwasher/driers, rice cookers, pots, pot lids, IH heaters, washing machines, vacuum cleaners, lighting apparatuses (lamps, apparatus bodies, shades, and the like), sanitary products, toilets, washbowls, mirrors, bathrooms (walls, ceilings, floors, and the like), building materials (interior walls, ceiling materials, floors, exterior walls, and the like), interior products (curtains, carpets, tables, chairs, sofas, shelves, beds, beddings, and the like), glasses, sashes, hand rails, doors, knobs, clothes, filters used for home electric appliance or the like, stationery, kitchen utensils, members used in the inside space of a car, and the like. When the tungsten oxide based particles have the photocatalytic performance, the photocatalyst effect can be given to the product. Examples of the substrate to be applied include a glass, a ceramic, a plastic, a resin such as acrylic resin, a paper, a fiber, a metal, a wood, and the like.

When a fiber is used as the substrate, as a fiber material there is used a synthetic fiber such as polyester, nylon, or acrylic fiber, a regenerated fiber such as rayon, a natural fiber such as cotton, wool, or silk, a combined fiber, a union cloth, a blended fiber of them, or the like. The fiber material may be in a loose fiber form. The fiber may have any form such as textile, knitting, or nonwoven fabric, or may be one on which ordinary dyeing or printing is performed. When the aqueous dispersion liquid is applied to the fiber material, a useful method is to use the tungsten oxide based particles together with a resin binder for fixing it to the fiber material.

As the resin binder, a resin of water soluble type, water dispersible type, or solvent soluble type can be used. Specifically, a melamine resin, an epoxy resin, a urethane resin, an acrylic resin, a fluorocarbon resin, or the like is used, but it is not limited to them. When the tungsten oxide based particles are fixed to the fiber material using the aqueous dispersion liquid, for example, the aqueous dispersion liquid is mixed with a resin binder of water dispersible type or water soluble type to produce a resin liquid, and the fiber material is dipped in this resin liquid and is thereafter wringed by a mangle roller and dried. By thickening the resin liquid, it can be coated on one side of the fiber material with a publicly known apparatus such as a knife coater. It is also possible to use a gravure roller to make the tungsten oxide based particles adhere to one side or both sides of the fiber material.

When the tungsten oxide based particles are made to adhere to the fiber surface using the aqueous dispersion liquid, if the adhering amount is too small, it is not possible for the tungsten oxide based particles to sufficiently exhibit the gas decomposing performance and the antibacterial performance which they have. If the adhering amount is too large, the performance which the tungsten oxide based particles have is exhibited, but the aesthetic property as the fiber material may decrease. Accordingly, preferably an appropriate adhesion amount is selected depending on the material or application. When the tungsten oxide based particles contained in the aqueous dispersion liquid have the photocatalytic performance under irradiation with visible light, clothes and interior goods using a fiber with the tungsten oxide based particles adhering on its surface is capable of exhibiting an excellent odor eliminating effect and antibacterial effect under irradiation with visible light in an indoor environment.

As described above, also when the dispersion agent is not used, the aqueous dispersion liquid of this embodiment excels in dispersibility of the tungsten oxide based particles. Thus, the tungsten oxide based particles do not precipitate for a long time, and stable liquidity can be maintained. Therefore, using the aqueous dispersion liquid or the coating material as such enables to provide a uniform and smooth film, and a product having such a film. Moreover, when the tungsten oxide based particles having the photocatalytic performance are used, it becomes possible to provide a photocatalyst film having photocatalytic performance such as excellent organic gas decomposing performance, hydrophilicity, antibacterial/disinfection performance, and the like, and further a product having this film.

EXAMPLES

Next, specific examples will be described. Note that in the examples below, as a method of producing a powder, there is used a method applying inductively coupled plasma processing in the sublimation process, but it is not limited to this method.

Example 1

First, the tungsten trioxide powder with a mean particle diameter of 0.5 μm was prepared as a raw material powder. This raw material powder was sprayed with carrier gas (Ar) on RF plasma, and further, as reaction gas, argon was supplied at a flow rate of 40 L/min and oxygen at a flow rate of 40 L/min. In this manner, the sublimation process of subjecting the raw material powder to oxidation reaction while sublimating it was carried out to produce a tungsten oxide powder. The tungsten oxide powder was heat treated under conditions of 900° C.×1.5 h in the atmosphere.

The mean primary particle diameter (D50) and the BET specific surface area of the tungsten oxide powder were measured. The mean primary particle diameter was measured by image analysis of a TEM picture. For TEM observation, H-7100FA made by Hitachi was used, an enlarged picture was subjected to image analysis and 50 particles or more were extracted, and integrated diameters with reference to volumes were obtained to calculate the D50. Measurement of the BET specific surface area was performed using a specific surface area measuring apparatus Macsorb 1201 made by Mountech. Preprocessing was carried out under conditions of 200° C.×20 minutes in nitrogen. Measurement results of the mean primary particle diameter (D50) and the BET specific surface area are shown in Table 1.

Next, the aqueous dispersion liquid was produced using the obtained tungsten oxide powder. The tungsten oxide powder was dispersed in water so that the concentration thereof becomes 10 mass %. Adjustment was made using water, sulfuric acid, and TMAH so that the pH of the dispersion water becomes 4.5. The dispersion processing was carried out using a beads mill. Measurement results of concentration and pH of the thus produced aqueous dispersion liquid are shown in Table 1.

Dispersibility of the aqueous dispersion liquid was estimated. The estimation of dispersibility was carried out just after the dispersion liquid was produced and after the liquid was left for two months. The dispersibility was estimated based on the D90 diameter of a particle size distribution and visual check of a precipitation state. Results thereof are shown in Table 2. The D90 diameter of the particle size distribution was measured using Microtrack MT3300 (laser diffraction particle size distribution analyzer) made by Nikkiso. When the maximum particle diameter is 6 μm or smaller, measurement was performed using Nanotrack UPA-EX made by Nikkiso. Also in this case, substantially equivalent data were obtained. The visual state check was evaluated based on the presence of precipitated particles. Results of the visual observation are shown in Table 2 as (D) when particles are precipitated, (C) when particles are precipitated slightly, (B) when no particles are precipitated, and (A) when no particles are precipitated and there is no difference in concentration between an upper and lower portions.

Example 2

The tungsten oxide powder was produced through the sublimation process similar to that of Example 1 except that oxygen is supplied at a flow rate of 80 L/min as reaction gas, and the pressure in the reaction container is adjusted to 25 kPa that is the decompression side. Further, using the obtained tungsten oxide powder, the aqueous dispersion liquid was produced similarly to Example 1. Measurement and evaluation similar to those in Example 1 were performed on the tungsten oxide powder and the aqueous dispersion liquid. Powder properties and dispersion liquid properties are shown in Table 1. Moreover, stability of the aqueous dispersion liquid was measured and evaluated similarly to Example 1. Evaluation results are shown in Table 2.

Example 3

The tungsten oxide powder was produced similarly to Example 1 except that heat treatment of the tungsten oxide powder is performed under conditions of 500° C.×2 h in the atmosphere. Next, using the obtained tungsten oxide powder, the aqueous dispersion liquid was produced similarly to Example 1. Properties of the tungsten oxide powder and the aqueous dispersion liquid are shown in Table 1. Moreover, stability of the aqueous dispersion liquid was measured and evaluated similarly to Example 1. Evaluation results are shown in Table 2.

Examples 4 to 14

In Example 4, the dispersion processing of the tungsten oxide powder in Example 2 was performed under conditions which cause the D90 diameter to be small, so as to produce the aqueous dispersion liquid. In Examples 5 to 7, the aqueous dispersion liquid was produced using the tungsten oxide powder of Example 3 while adjusting its concentration to be in the range of 0.5 mass % to 20 mass %. In Example 8, the aqueous dispersion liquid was produced using the tungsten oxide powder produced similarly to Example 1 except that heat treatment is performed under conditions of 850° C.×1.5 h in the atmosphere. In Examples 9 and 10, the aqueous dispersion liquid was produced similarly to Example 6 except that the adjustment value of pH is changed.

In Example 11, the aqueous dispersion liquid was produced similarly to Example 6 except that a raw material containing a large amount of Fe and Mo is used as the raw material powder in the sublimation process. The content of Fe in the tungsten oxide composite powder was 300 ppm. In Example 12, the aqueous dispersion liquid was produced similarly to Example 6 except that zirconium oxide powder is mixed in the raw material powder to be used in the sublimation process. The content of Zr in the tungsten oxide composite powder was 1000 ppm. In Example 13, the aqueous dispersion liquid was produced similarly to Example 6 except that platinum powder is mixed in the raw material powder to be used in the sublimation process. The content of Pt in the tungsten oxide composite powder was 1000 ppm. In Example 14, the aqueous dispersion liquid was produced similarly to Example 6 except that water containing 10 mass % of alcohol is used as the dispersion medium.

Dispersion stability of the aqueous dispersion liquids of Examples 4 to 14 was measured and evaluated similarly to Example 1. Results thereof are shown in Table 2.

As is clear from Table 2, in the aqueous dispersion liquids of Examples 1 to 3, there were ones with a relatively large D90 diameter based on the dispersion conditions, and slight precipitation was recognized in the dispersion liquids. However, after two months, they changed slightly and were relatively stable. All the aqueous dispersion liquids of Examples 4 to 14 had a small D90 diameter, and exhibited good properties while having no precipitation. Moreover, almost no precipitation occurred after two months and there were small changes in particle diameters, and thus excellent stability was recognized. These dispersion liquids exhibited similar states after it was stored for three months, and it was recognized that they are stable for a long period. In addition, when the adjustment range of pH is close to strongly acidic side or neutral, the liquids were relatively uniform and stable just after the dispersion, but precipitation was seen, although it was small, after two months.

Comparative Example 1

An aqueous dispersion liquid was produced under conditions similar to those of Example 6 except that the adjustment range of pH is changed to the strongly acidic side. The pH of the aqueous dispersion liquid was 0.5, and slight precipitation was seen just after dispersion. After it was stored for two months, the precipitation advanced further and the precipitation amount increased. It is conceivably due to that the zeta potential became close to zero and it became liable to precipitate.

Comparative Example 2

A dispersion liquid was produced under conditions similar to those of Example 6 except that the concentration of the tungsten oxide powder is 50 mass % and the adjustment range of pH is changed to be close to the vicinity of neutral. The pH of the aqueous dispersion liquid was 7.1, and the tungsten oxide dissolved.

Comparative Example 3

A tungsten oxide powder which is commercially available (made by Raremetallic) as a reagent was used to produce an aqueous dispersion liquid having concentration of 10 mass % and pH of 5.2. The particle diameter of the tungsten oxide powder is too large and hence it does not disperse in water sufficiently, and it was recognized that there is large precipitation.

TABLE 1

| | POWDER PROPERTIES | | DISPERSION LIQUID PROPERTIES | |
| --- | --- | --- | --- | --- |
| | MEAN PARTICLE DIAMETER (D50) [nm] | BET SPECIFIC SURFACE AREA [m$^2$/g] | CONCEN- TRATION [MASS %] | pH |
| EXAMPLE 1 | 195 | 3.9 | 10 | 4.5 |
| EXAMPLE 2 | 4 | 201 | 10 | 3.8 |
| EXAMPLE 3 | 25 | 35 | 10 | 4.2 |
| EXAMPLE 4 | 4 | 201 | 10 | 4.5 |
| EXAMPLE 5 | 25 | 35 | 0.5 | 4.5 |
| EXAMPLE 6 | 25 | 35 | 10 | 4.0 |
| EXAMPLE 7 | 25 | 35 | 20 | 3.4 |
| EXAMPLE 8 | 95 | 8.5 | 10 | 4.0 |
| EXAMPLE 9 | 25 | 35 | 10 | 2.2 |
| EXAMPLE 10 | 25 | 35 | 10 | 6.4 |
| EXAMPLE 11 | 25 | 35 | 10 | 4.2 |
| EXAMPLE 12 | 25 | 36 | 10 | 4.1 |
| EXAMPLE 13 | 25 | 35 | 10 | 4.0 |
| EXAMPLE 14 | 25 | 35 | 10 | 3.4 |
| COMPARATIVE EXAMPLE 1 | 25 | 35 | 10 | 0.5 |
| COMPARATIVE EXAMPLE 2 | 25 | 35 | 50 | 7.1 |
| COMPARATIVE EXAMPLE 3 | 1210 | 0.7 | 10 | 5.2 |

TABLE 2

DISPERSION STABILITY OF DISPERSION LIQUIDS
(CONTACT ANGLE MEASUREMENT RESULTS)

| | JUST AFTER DISPERSION | | AFTER 2 MONTHS | |
|---|---|---|---|---|
| | D90 [nm] | VISUAL EVALUATION* | D90 [nm] | VISUAL EVALUATION* |
| EXAMPLE 1 | 15 | (C) | 16 | (D) |
| EXAMPLE 2 | 12 | (C) | 13 | (D) |
| EXAMPLE 3 | 0.110 | (A) | 0.130 | (A) |
| EXAMPLE 4 | 0.085 | (A) | 0.090 | (A) |
| EXAMPLE 5 | 0.090 | (A) | 0.091 | (A) |
| EXAMPLE 6 | 0.097 | (A) | 0.098 | (A) |
| EXAMPLE 7 | 0.100 | (A) | 0.100 | (A) |
| EXAMPLE 8 | 0.950 | (A) | 0.965 | (A) |
| EXAMPLE 9 | 0.099 | (B) | 0.110 | (C) |
| EXAMPLE 10 | 0.089 | (B) | 0.095 | (B) |
| EXAMPLE 11 | 0.097 | (A) | 0.100 | (A) |
| EXAMPLE 12 | 0.095 | (A) | 0.102 | (A) |
| EXAMPLE 13 | 0.090 | (A) | 0.099 | (A) |
| EXAMPLE 14 | 0.099 | (A) | 0.103 | (A) |
| COMPARATIVE EXAMPLE 1 | 0.240 | (C) | 0.420 | (D) |
| COMPARATIVE EXAMPLE 2 | — | DISSOLVED | — | — |
| COMPARATIVE EXAMPLE 3 | 65 | (D) | 66 | (D) |

*(A): NO PRECIPITATION, NO CONCENTRATION DIFFERENCE BETWEEN UPPER AND LOWER PORTIONS (B): NO PRECIPITATION (C): SLIGHTLY PRECIPITATED (D): PRECIPITATED

Example 15

In the aqueous dispersion liquid obtained in Example 6, 1 mass % of colloidal silica was mixed with the tungsten oxide powder to produce a water based coating material. Dispersibility of this coating material was evaluated just after it was produced and after it was stored for two months. Results thereof are shown in Table 3. The water based coating material of Example 15 is a uniform dispersion liquid with no precipitation of particles similarly to the aqueous dispersion liquid, and it was recognized that it is stable even when it is stored for a long period.

Comparative Example 4

Dispersibility of a coating material including a commercially available titanium oxide was evaluated when it was purchased and after it was stored for two months. Results thereof are shown in Table 3. In the commercially available coating material, a time already elapsed from production, and slight precipitation of particles was recognized. Further, after it was stored for two months, aggregation advanced and precipitated particles increased.

TABLE 3

DISPERSION STABILITY OF DISPERSION LIQUIDS
(CONTACT ANGLE MEASUREMENT RESULTS)

| | JUST AFTER DISPERSION | | AFTER 2 MONTHS | |
|---|---|---|---|---|
| | D90 [nm] | VISUAL EVALUATION* | D90 [nm] | VISUAL EVALUATION* |
| EXAMPLE 15 | 0.115 | (A) | 0.120 | (A) |
| EXAMPLE 4 | 0.110 | (C) | 0.180 | (D) |

Example 16

The water based coating material of Example 15 was applied on the surface of a glass and dried to thereby produce a glass having a tungsten oxide coating layer on its surface. On the surface of this glass, presence of rough particles and aggregated particles was checked visually, but no existence of rough particles and aggregated particles was recognized. It was recognized that a uniform film is obtained. Moreover, when arbitrary portions were observed via a microscope, it was recognized that an even film was formed in each portion.

Example 17

A photocatalyst film was formed on a glass surface using the aqueous dispersion liquid of Example 6. The photocatalytic performance of this photocatalyst film under irradiation with visible light was evaluated. The photocatalytic performance was evaluated by measuring a decomposition rate for acetaldehyde gas. Specifically, a distribution type apparatus similar to the one for removal performance (decomposing performance) evaluation for nitrogen oxide of JIS-R-1701-1 (2004) was used to measure the gas decomposition rate under conditions described below. Moreover, when it is represented by the L*a*b color system, the aqueous dispersion liquid had a color with a* of −14, b* of 15, and L* of 80. The aqueous dispersion liquid as such attains the photocatalytic performance when being applied on a substrate, but does not impair the color of the substrate.

A decomposition test for acetaldehyde gas was performed as follows. The initial concentration of acetaldehyde is 10 ppm, the gas flow rate is 140 mL/min, and a sample amount is 0.2 g. The sample is adjusted such that it is applied on a glass plate of 5 cm×10 cm and dried. Preprocessing is irradiation with black light for 12 hours. A white fluorescent light (FL20SS W/18, made by Toshiba Lighting & Technology) is used as a light source, and an ultraviolet cutting filter (Kralex N-169, made by Nitto Jushi Kogyo) is used to cut wavelengths under 380 nm. Illuminance is adjusted to 1000 lx. First, irradiation with light is not performed, and it is waited until gas absorption ceases and the gas becomes stable. Irradiation with light is started after it becomes stable. Under such conditions, irradiation with light is performed, the gas concentration after 15 minutes elapses is measured, and a gas decomposition rate is obtained. However, when the gas concentration does not become stable even after 15 minutes elapse, the concentration is measured continuously until it becomes stable.

The gas concentration before the light irradiation is denoted by A, the gas concentration when 15 minutes elapse from the light irradiation and it becomes stable is denoted by B, and a value calculated based on [Formula: (A−B)/A×100] from these gas concentration A and gas concentration B is assumed as the gas decomposition rate (%). As the gas analyzing apparatus, Multi-gas Monitor 1412 made by INOVA was used. As a result of performing such measurement, it was recognized that the photocatalytic performance is stably exhibited. This is because the produced tungsten oxide powder itself has the photocatalytic performance, and by performing the dispersion processing under conditions which do not cause decrease in activity of the powder, it is possible to exhibit the photocatalytic performance even in a dispersion liquid and a coating material.

Example 18

The aqueous dispersion liquid of Example 6 was mixed with a resin liquid of acrylic resin, and a plain weave fabric formed of polyester weighing 150 g/m² was dipped in this mixed liquid (coating material), so as to produce a polyester fiber to which the tungsten oxide photocatalyst is adhered. A sample of 5 cm×10 cm was cut from each of the fiber to which the photocatalyst is adhered and a fiber to which no photocatalyst is adhered, and the photocatalytic performance under irradiation with visible light was evaluated with each of them by a method similar to that in Example 17. As a result, it was recognized that the polyester fiber to which the photocatalyst is adhered is higher in decomposition rate for acetaldehyde gas than the fiber to which it is not adhered. Further, 10 similarly produced samples were prepared and dispersion in performance was evaluated, and it was recognized that the adhesion amount of the photocatalyst to the fiber is stable since the dispersion liquid of this example has excellent dispersibility. Further, it was recognized that the polyester fiber retains a uniform aesthetic property.

Example 19

The aqueous dispersion liquid with pH 4 produced in Example 6 was applied on a silicon substrate, and dried under conditions of 150° C.×10 minutes, so as to produce a film. Existence of surface hydroxyl was checked by a transmission method with FT-IR (Fourier-transform infrared absorption spectroscopy/apparatus name: IFS66v made by BRUKER), and a peak originated in hydroxyl in the vicinity of 3700 cm$^{-1}$ was recognized. Moreover, the dispersion liquid was applied on the glass substrate (5 cm×10 cm), and dried under conditions of 150° C.×10 minutes, so as to produce a film with an adhesion amount of the tungsten oxide of 0.1 g/50 cm². The photocatalytic performance of this film was evaluated by a method similar to that in Example 17. A preprocessing by black light was performed for one hour, and the irradiation intensity of the visible light was 6000 lx. The gas decomposition rate was 80.1%.

Further, the zeta potential of the dispersion liquid was measured. For measuring the zeta potential, ELSZ-2 and pH Titrator System (ELSZ-PT) made by Otsuka Electronics were used. As pH adjusters, an HCl aqueous solution of 0.1 mol/L was used for adjusting acidity, and NaOH of 0.1 mol/L was used for adjusting alkalinity. The dispersion liquid diluted to 0.1 mass % is adjusted to pH 2, 3, 4, 5, 6, and 7 by the pH Titrator, and thereafter the zeta potential was measured with each pH. The zeta potential with pH 4 was −29.9 mV. Results thereof are shown in Table 4.

Example 20

The pH of the aqueous dispersion liquid obtained in Example 6 was adjusted by TMAH, so as to produce a dispersion liquid with pH 6. This dispersion liquid was applied on a silicon substrate and dried under conditions of 150° C.×10 minutes, so as to produce a film. Similarly to Example 19, existence of surface hydroxyl was checked with the FT-IR, and it was recognized that a peak originated in hydroxyl in the vicinity of 3700 cm$^{-1}$ is largely decreased. Moreover, the decomposition rate for acetaldehyde gas was measured similarly to Example 19 using the dispersion liquid adjusted to pH 6, and the gas decomposition rate was 54%. The zeta potential with pH 6 was −32.3 mV. Results thereof are shown in Table 4. It is conceivable that hydroxyl on the surfaces of the tungsten oxide particles decreases by adjusting the pH to 6, and decrease of the gas decomposition rate occurs.

Example 21

The pH of the aqueous dispersion liquid obtained in Example 6 was adjusted with sulfuric acid, so as to produce a dispersion liquid with pH 2. The dispersion liquid was applied on a silicon substrate and dried under conditions of 150° C.×10 minutes, so as to produce a film. Similarly to Example 19, existence of surface hydroxyl was checked with the FT-IR, and a peak originated in hydroxyl in the vicinity of 3700 cm$^{-1}$ was recognized. Moreover, the decomposition rate for acetaldehyde gas was measured similarly to Example 19 using the dispersion liquid adjusted to pH 2, and the gas decomposition rate was 61.1%. The zeta potential with pH 2 was −7.9 mV. Results thereof are shown in Table 4. By adjusting to pH 2, the zeta potential in the aqueous dispersion liquid was decreased. Accordingly, the particles tend to aggregate. It is conceivable that the specific surface area decreases by aggregation of the particles, and thus decrease of the gas decomposition rate occurs.

TABLE 4

| | | FILM PROPERTIES | | |
| --- | --- | --- | --- | --- |
| | DISPERSION LIQUID pH | FTIR PEAK NEAR 3700 cm$^{-1}$ | GAS DECOMPOSITION RATE (%) | ZETA POTENTIAL (mV) |
| EXAMPLE 19 | 4 | (B) | 80.1 | −29.9 |
| EXAMPLE 20 | 6 | (D) | 54.0 | −32.3 |
| EXAMPLE 21 | 2 | (B) | 61.1 | −7.9 |

Example 22

The coating material produced in Example 15 was applied on a glass of the interior space of an automobile to form a photocatalyst film, and this caused decrease in cigarette odor and prevented the glass from being soiled easily. Incidentally, when hydrophilicity of the glass on which this coating material is applied was evaluated, the contact angle was 1° or smaller, and superhydrophilicity was exhibited. Moreover, evaluation of antibacterial performance was performed using aureus bacteria, colon bacillus, and mold, and it was recognized that excellent antibacterial performance is exhibited against all of them.

The aqueous dispersion liquids using the tungsten oxide based particles of the above-described respective examples have excellent dispersibility, and hence are capable of providing a uniform film. Since the tungsten oxide based particles have the photocatalytic performance, the decomposing performance for organic gas such as acetaldehyde can be obtained stably, and moreover, visual problems of color unevenness and the like do not occur easily. Thus, the liquids can be used preferably for members used in the interior space of an automobile, building materials and interior materials used in factories, shops, schools, public facilities, hospitals, welfare facilities, accommodations, houses, and the like, and home electronic appliances, and the like.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and sprit of the inventions.

What is claimed is:

1. A method for producing a film, comprising:
applying an aqueous dispersion liquid or a coating material comprising the aqueous dispersion liquid and at least one binder component selected from an inorganic binder and an organic binder on a substrate to form an applied film of the aqueous dispersion liquid or the coating material; and
drying the applied film to produce the film,
wherein the aqueous dispersion liquid comprises particles selected from tungsten oxide particles and tungsten oxide composite particles and a dispersion medium including water,
wherein a mean primary particle diameter (D50) of the particles is in a range of 1 nm to 400 nm, a concentration of the particles in the aqueous dispersion liquid is in a range of 0.1 mass % to 40 mass %, and pH of the aqueous dispersion liquid is in a range of 1.5 to 6.5, and
wherein the tungsten oxide composite contains at least one metal element selected from transition metal elements and aluminum, or a compound including at least one metal element selected from transition metal elements and aluminum, in a range of 0.001 mass % to 50 mass % as an amount of the metal element, balanced by tungsten oxide.

2. The producing method according to claim 1, wherein the dispersion medium contains alcohol in a range of 20 mass % or less.

3. The producing method according to claim 1, wherein the coating material contains the binder component in a range of 5 mass % to 95 mass %.

4. The producing method according to claim 1, wherein the concentration of the particles in the aqueous dispersion liquid is in a range of 1.0 mass % to 20 mass %, and pH of the aqueous dispersion liquid is in a range of 2.5 to 5.5.

5. The producing method according to claim 1, wherein a D90 diameter of a particle size distribution of the particles in the aqueous dispersion liquid is in a range of 0.01 μm to 10 μm.

6. The producing method according to claim 1, wherein the metal element is at least one element selected from titanium, zirconium, manganese, iron, palladium, platinum, copper, silver, aluminum, and cerium.

7. The producing method according to claim 1, wherein the tungsten oxide composite contains the metal element or the compound in a range of 0.01 mass % to 10 mass % as the amount of the metal element.

* * * * *